United States Patent [19]

Koseki et al.

[11] Patent Number: 5,112,994
[45] Date of Patent: * May 12, 1992

[54] METHOD OF PRODUCING (S)-4-HYDROXYMETHYL-γ-LACTONE

[75] Inventors: Koshi Koseki; Takashi Ebata; Hiroshi Kawakami; Hajime Matsushita, all of Yokohama; Kazuo Itoh; Yoshitake Naoi, both of Tokyo, all of Japan

[73] Assignees: Japan Tobacco Inc.; Yuki Gosei Kogyo Co., Ltd., Tokyo, Japan

[*] Notice: The portion of the term of this patent subsequent to Feb. 19, 2008 has been disclaimed.

[21] Appl. No.: 583,647

[22] Filed: Sep. 17, 1990

[30] Foreign Application Priority Data

Sep. 22, 1989 [JP] Japan .................. 1-244945

[51] Int. Cl.$^5$ .......................... C07D 307/78
[52] U.S. Cl. .................................. 549/323
[58] Field of Search ........................... 549/323

[56] References Cited

U.S. PATENT DOCUMENTS

| | | | |
|---|---|---|---|
| 3,926,947 | 12/1975 | Lipska | 260/209 R |
| 4,673,759 | 6/1987 | Dalcanale | 549/323 |
| 4,959,161 | 9/1990 | Clubley | 549/323 |
| 4,994,585 | 2/1991 | Koseki et al. | 549/323 |

FOREIGN PATENT DOCUMENTS 0411403  2/1991  European Pat. Off. .

OTHER PUBLICATIONS

Tetrahedron, "Stereoselective Synthesis of D-Ribose from L-Glutamic Acid", vol. 30, No. 19, 1974, pp. 3547–3552, M. Taniguchi et al.

Journal of Organic Chemistry, "Synthesis of the Dideoxynucleosides ddC and CNT from Glutamic Acid, . . .", vol. 53, 1988, pp. 4780–4789, Masami Okabe et al.

Heterocycles, "A Method for Easy Preparation of Optically Pure (S)-5-Hydroxy-2-Penten-4-Olide and (S)-5-Hydroxy . . .", vol. 30, No. 3, 1990, pp. 423–426, Koshi Koseki et al.

Lipska et al., J. of App. Polymer Sci., vol. 15, pp. 419–435 (1971).

Halpern et al., J. Org. Chem., vol. 28, No. 2, pp. 204–209 (1973).

*Primary Examiner*—C. Warren Ivy
*Assistant Examiner*—Raymond Covington
*Attorney, Agent, or Firm*—Birch, Stewart, Kolasch & Birch

[57] ABSTRACT

(S)-4-hydroxymethyl-γ-lactone is prepared by oxidizing dihydrolevoglucosenone with a peracid in an organic solvent. (S)-4-hydroxymethyl-γ-lactone is prepared from levoglucosenone. First, levoglucosenone is catalytic hydrogenated, thereby dihydrolevoglucosenone is obtained. Next, dihydrolevoglucosenone thus obtained is oxidized with a peracid in an organic solvent, thereby (S)-4-hydroxymethyl-γ-lactone is obtained. In this manner, (S)-4-hydroxymethyl-γ-lactone can be obtained with high optical purity.

11 Claims, No Drawings

METHOD OF PRODUCING (S)-4-HYDROXYMETHYL-γ-LACTONE

BACKGROUND OF THE INVENTION

1. Field of the Invention

The present invention relates to a method of producing (S)-4-hydroxymethyl-γ-lactone represented by the following chemical structural formula 10.

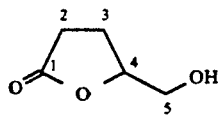

2. Description of the Related Art (S)-4-hydroxymethyl-γ-lactone 10 is a useful raw material for synthesizing various kinds of nucleic acids. The nucleic acids are excellent fodder additives, and some of then are even useful as medicines.

In order to synthesize (S)-4-hydroxymethyl-γ-lactone 10, the below-illustrated method, which begins with glutamic acid as the starting material, is presently known (J.Org.Chem.,Vol.53, No.20, p4781(1988)).

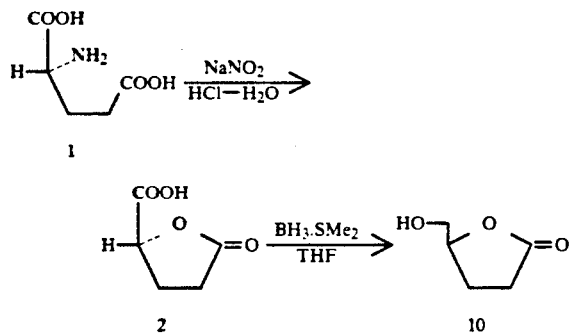

However, this method has the following problems:

As illustrated above, in the first step of this method, glutamic acid 1 is subjected to deamination, and thus forming crystalline intermediate 2. Since the retention of the stereochemistry of the intermediate 2 during this reaction is not sufficient, the intermediate partially becomes a recemate. Since the reaction proceeds via this intermediate 2, it is extremely difficult to obtain, the (S)-4-hydroxymethyl-γ-lactone 10, with the high optical purity.

Further, the yield of intermediate 2 from glutamic acid 1 is 56%, and the yield of (S)-4-hydroxymethyl-γ-lactone from intermediate 2 is no more than about 63%. Therefore, the yield of the objective material 10 as a result is extremely low.

Moreover, since the crystalline intermediate 2 is soluble to water, it is very difficult to isolate it, and the procedures thereof is very complicated.

In addition, since not only because of its low yield, but also because of the high price of the raw material, namely glutamic acid, the cost of the product becomes very expensive.

SUMMARY OF THE INVENTION

The purpose of the present invention is to provide an easy and inexpensive method of producing (S)-4-hydroxymethyl-γ-lactone (to be called an objective compound hereinafter) with the high optical purity.

This purpose can be achieved by oxidizing dihydrolevoglucosenone with a peracid in an organic solvent.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

In order to provide an easy and inexpensive method of preparing (S)-4-hydroxymethyl-γ-lactone with high optical purity, the inventors conducted many studies and tests, and they invented a method of preparing the objective compound using dihydrolevoglucosenone as the raw material. More particular, the purpose of the present invention can be achieved by oxidizing dihydrolevoglucosenone with a peracid in an organic solvent.

The dihydrolevoglucosenone used as the starting material in the present invention can be obtained by adding hydrogen to the double bond of levoglucosenon based on the catalytic hydrogenation or the like.

Levoglucosenone is a well-known material, and a great amount of it can be easily obtained by thermally decomposing cellulose at low-cost. Further, a particular L-isomer thereof can be obtained with a high optical purity. Therefore, by hydrogenating the levoglucosenone thus obtained, a high optically pure dihydrolevoglucosenone can be obtained.

Some of the examples of peracid used for oxidizing the above dihydrolevoglucosenone in the present invention are: performic acid, peracetic acid, perbenzoic acid, perphthalic acid, metachloroperbenzoic acid, and magnesium monoperoxyphthalate hexahydrate. Off course, many other peracids can be used in the present invention.

In the present invention, dihydrolevoglucosenone is reacted with the peracid in an equimolar amount. Therefore, the amount of the peracid used for 1 mole of dihydrolevoglucosenone is 1 mole, which is theoretically sufficient. However, in practice, it is desirable to use 1.0–3.0 moles of the peracid for 1 mole of dihydrolevoglucosenone.

In the present invention the oxidation of dihydrolevoglucosenone is carried out in the liquid phase. Thus, the present invention requires a dihydrolevoglucosenone solution, and in order to prepare it, an ordinary organic solvent may be used. Some examples of the organic solvent are acetic acid, methylene chloride, methanol, and the like. Criteria for selecting the solvent are: the solvent well desolves dihydrolevoglucosenone; it does not react with a peracid; it does not produce byproducts which complicate the care after the reaction; and the like. Any solvent, in fact, can be used if it satisfies the above criteria.

The synthesis path from levoglucosenone to the objective compound according to the method of the present invention is shown as follows:

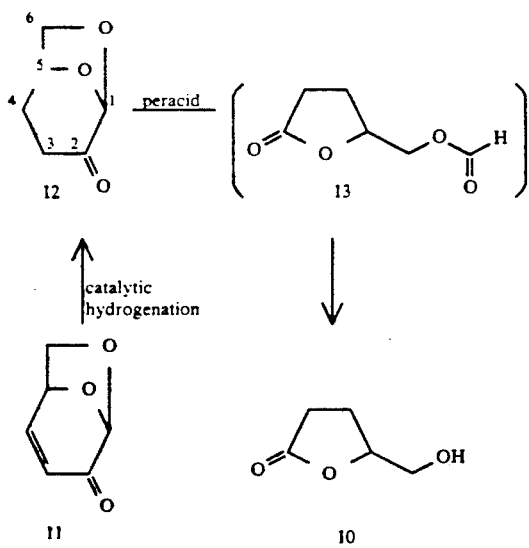

The catalytic hydrogenation to prepare dihydrolevoglucosenone 12 from levoglucosenone 11 can be carried out under the general condition for the hydrogenation. Some of the examples of the catalysts and the solvents are:

| Catalysts | Solvents |
| --- | --- |
| Raney Ni W2 | ethanol |
| 5% Pd/BaSO4 | dioxane |
| PtO2 | diethyl ether |

[Shinjikkenkagakukoza, (New Experimental Chemistry Lectures) Vol. 15, II, p 390]

The oxidizing reaction using the above peracids can be performed in an extremely simple procedure. That is, a peracid is added to the solution of dihydrolevoglucosenone 12, and the solution is stirred at room temperature for a day or two days to complete the reaction. After the reaction is completed the remaining peracid in the reaction products is removed, thereby obtaining the objective compound 10 in a high yield.

The objective compound 10 thus obtained can be used as a raw material for synthesizing nucleic acids and the like, or fodder, as stated in the beginning of this specification. Or, the objective compound can be further purified by means of the silica gel chromatography, etc. in order to obtain the objective compound with even the higher-purity. Methods of synthesizing nucleic acids from the objective compound are described in, for example, the following publications.

* synthesis of ddC:
M. Okabe et al., J.Org.Chem.,53, p4780 (1988)
* synthesis of ddC, ddI, and ddA:
V. Farina et al., Tetrahedron Lett.,29, p1239 (1988)

In addition, intermediate 13 produced during the oxidation reaction in the above synthesis path is relatively stable, and can be isolated if needed so.

The method of the present invention will be described in more detail by way of examples thereof.

EXAMPLE 1

Catalytic Hydrogenation of Levoglucosenone 8g (63.5mmole) of levoglucosenone was dissolved into 80ml of ethyl acetate. After adding 5%Pd-C (0.5g) thereto, the catalytic hydrogenation of levoglucosenone was carried out by stirring it at room temperature under hydrogen atmosphere. Then, the catalyst was filtered off, and the reaction solution was condensed. Further, the solution was distilled at temperature of 62°-64° C. under reduce pressure of 2Torr, thereby obtaining 7.32g of the product (90.1% yield).

The product was analyzed by IR spectrum as well as NMR spectrum, and was proved to be dihydrolevoglucosenone. The results were as follows:

IR spectrum (cm$^{-1}$)

$\mu$mafilm 2970, 2920, 1740, 1110, 990, 910, 880 max

| $^1$H-NMR spectrum ($\delta$ppm/CDCl$_3$) |
| --- |
| 2.03 (1H, dd, J = 8.0, 10.2 Hz) |
| 2.33 (2H, m) |
| 2.66 (1H, m) |
| 3.98 (1H, ddd, J = 1.4, 5.0, 7.0 Hz, H-6) |
| 4.09 (1H, dd, J = 0.8, 7.5 Hz, H-6) |
| 4.72 (1H, bs, H-5) |
| 5.12 (1H, s, H-1) |

Oxidation of Dihydrolevoglucosenone 7.32g (57.2mmole) of dihydrolevoglucosenone obtained in the above was dissolved into 25ml of acetic acid, and then 8ml of 40% peracetic acid was added dropwise while the solution was cooled by ice. Since the addition of the peracetic acid raises the temperature of the solution, therefore the addition was carried out gradually over the period of an hour, maintaining the temperature at 25°-30° C. After stirring the solution for an hour at room temperature, disappearance of the raw material was confirmed by using TLC (hexane : ethyl acetate=1:1). Next, the remaining amount of the peracetic acid was measured by KI-sodium thiosulfate method (Shinjikkenkagakukoza vol.15, I-2, p742), and an amount of dimethyl sulfide which is equivalent to that of the remaining peracetic acid is added to the solution. After stirring the resultant solution for an hour at room temperature, 20ml of 1N hydrochloric acid is added thereto and the solution was further stirred over night. Then, the resultant solution was condensed under vacuum pressure, and 100ml of methanol and 2ml of conc. hydrochloric acid are added to the solution. The resultant solution was heated to 50° C., and stirred for 3 hours. The resultant solution was further condensed under vacuum pressure, thereby obtaining 6.7 g of oil-like product, the objective compound (100% yield).

The product was analyzed by IR spectrum and NMR spectrum, and the following results were obtained. According to the NMR spectrum analysis, the purity of this product was 90% or more.

IR spectrum (cm$^{-1}$)

$\nu$film 3400, 2950, 1770, 1180, 1060 max

| $^1$H-NMR spectrum ($\delta$ppm/CDCl$_3$) |
| --- |
| 2.1–2.35 (2H, m) |
| 2.5–2.7 (2H, m) |
| 3.65 (1H, dd, H-5) |
| 3.82 (1H, dd, H-5) |
| 4.64 (1H, m, H-4) |

Confirmation of Structure of the Product by Benzoylation

The structure of the oil-like product obtained in the above experiment was confirmed as follows:

6.70 g of the oil-like product obtained was dissolved into 70ml of pyridine. Then, 8.85g (0.063mol) of benzoyl chloride was added to this solution, and the solution was stirred over night. After the resultant solution was condensed under vacuum pressure and pH of the solution was adjusted to 2, extraction with ethyl acetate was performed. This extracted solution was washed with 1N hydrochloric acid, water, sodium bicarbonate aqueous solution, water, and NaCl solution, in the mentioned order. The solution was dried using magnesium sulfate, then the solution was condensed, thereby obtaining 12.20g of product in the form of a solid material having an amorphous solid (97.3% yield from dihydrolevoglucosenone).

The above product was recrystallized from ether, and IR spectrum and NMR spectrum of the crystal were measured. The results were as shown below. The results coincided with the data described in a publication regarding the benzoate of the objective compound (M. Taniguchi et.al. Tetrahedron, 30,3547(1974)). With this fact, it is confirmed that the product prepared by the above oxidation reaction is really the objective compound of the present invention.

IR spectrum (cm$^{-1}$)

$\nu$film 1780, 1730 max

| $^1$H-NMR spectrum ($\delta$ppm/CDCl$_3$) |
| --- |
| 2.15 (1H, m) |
| 2.40 (1H, m) |
| 2.63 (2H, m) |
| 4.44 (1H, dd, J = 5.3, 12.3 Hz, H-5) |
| 4.55 (1H, dd, J = 3.2, 12.3 Hz, H-5) |
| 4.88 (1H, m, H-4) |
| 7.45 (2H, t, J = 7.5 Hz, m-H) |
| 7.59 (1H, t, J = 7.5 Hz, p-H) |
| 8.03 (2H, d, J = 7.5 Hz, o-H) |

Referencial Example (Isolation of Intermediate)

0.5g (3.91mmol) of dihydrolevoglucosenone obtained in the catalytic hydrogenation in Example 1 is dissolved into 2ml of acetic acid, and the reaction similar to example 1 was carried out using 40% peracetic acid (0.6ml). Then, water was added to the solution, and the solution was extracted by ethyl acetate. The ethyl acetate layer was washed with water, sodium hydrogensulfate aqueous solution, and sodium bicarbonate aqueous solution in the mentioned order. After that, the solution was dried using magnesium sulfate and then be condensed, thereby obtaining 130mg of oil-like product.

The results of IR spectrum and NMR spectrum analysis of the product were as follows:

IR spectrum (cm$^{-1}$)

$\nu$film: 2950, 1780, 1720, 1150, 1070, 940, 920

| $^1$H-NMR spectrum ($\delta$ppm/CDCl$_3$) |
| --- |
| 2.10 (1H, m) |
| 2.40 (1H, m) |
| 2.62 (2H, m) |
| 4.25 (1H, dd, J = 5.3, 12.2 Hz, H-5) |
| 4.45 (1H, dd, J = 3.2, 12.2 Hz, H-5) |
| 4.80 (1H, m, H-4) |
| 8.12 (1H, s, CHO) |

EXAMPLE 2

1 g (7.94mmole) of dihydrolevoglucosenone was dissolved into 9ml of methylene chloride, followed by addition of 5ml of methylene chloride into which 2.57g (11.9mmol) of metachloroperbenzoic acid was dissolved. The reaction was carried out with stirring the solution over night at room temperature. Next, the crystals precipitated in the solution were filtered off, and the filtrate was condensed. Then, 150ml of methanol and 1ml of conc. hydrochloric acid were added to the condensed filtrate, and the solution was stirred over night at 40° C. The resultant solution was further condensed, and 0.34g of oil-like product was obtained (40% yield).

The results of the analysis of the product by IR spectrum and NMR spectrum coincided with the data of the objective compound obtained in Example 1, and the product thus obtained was confirmed to be the objective compound.

EXAMPLE 3

0.5g (3.97mmol) of dihydrolevoglucosenone was dissolved into 5ml of methanol, and 18ml of methanol in which 2.36g (4.77mmol) of magnesium monoperoxyphthalate hexahydrate was suspended, was added to the above solution. The reaction was carried out with stirring the solution at room temperature over night. Then, the crystals precipitated in the reactant solution were filtered off, and the filtrate was condensed. 150ml of methanol and 1ml of conc. hydrochloric acid were added to the condensed filtrate, and this solution was stirred at 40° C. for two hours. The reactant solution was further condensed under vacuum pressure, and 0.19g of oil-like product was obtained (45% yield).

The results of the analysis of the product by IR spectrum and NMR spectrum coincided with the data of the objective compound obtained in Example 1, and the product thus obtained was confirmed to be the objective compound.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A method of producing (S)-4-hydroxymethyl-$\gamma$-lactone comprising a step of oxidizing dihydrolevoglucosenone with a peracid in an organic solvent, thereby obtaining (S)-4-hydroxymethyl-$\gamma$-lactone.

2. A method of producing (S)-4-hydroxymethyl-$\gamma$-lactone comprising steps of:
   catalytic-hydrogenating levoglucosenone, thereby obtaining dihydrolevoglucosenone; and
   oxidizing said dihydrolevoglucosenone with a peracid in an organic solvent, thereby obtaining (S)-4-hydroxymethyl-$\gamma$-lactone.

3. A method according to claim 1, wherein the peracid is selected from the group consisting of performic acid, peracetic acid, perbenzoic acid, perphthalic acid, metachloroperbenzoic acid, and magnesium monoperoxyphthalate hexahydrate.

4. A method according to claim 2, wherein the peracid is selected from the group consisting of performic acid, peracetic acid, perbenzoic acid, perphthalic acid, metachloroperbenzoic acid, and magnesium monoperoxyphthalate hexahydrate.

5. A method according to claim 1, wherein the organic solvent is selected from the group consisting of acetic acid, methylene chloride, and methanol.

6. A method according to claim 2, wherein the organic solvent is selected from the group consisting of acetic acid, methylene chloride, and methanol.

7. A method according to claim 1, wherein the oxidation is carried out at a temperature ranging from −20° to 100° C.

8. A method according to claim 2, wherein the oxidation is carried out at a temperature ranging from −20° to 100° C.

9. A method according to claim 1, wherein 1.0–3.0 moles of a peracid is used against 1 mole of dihydrolevoglucosenone.

10. A method according to claim 2, wherein 1.0–3.0 moles of a peracid is used against 1 mole of dihydrolevoglucosenone.

11. A method according to claim 2, wherein the catalytic hydrogenation is carried out by using a catalyst selected from the group consisting of Raney Ni, 5%Pd/BaSO$_4$, 5%Pd-C, and PtO$_2$.

* * * * *